United States Patent
Reisky et al.

(10) Patent No.: US 12,275,819 B2
(45) Date of Patent: Apr. 15, 2025

(54) PROCESS FOR THE DECOMPOSITION OF POLYETHER-POLYURETHANE

(71) Applicant: Covestro Intellectual Property GmbH & Co. KG, Leverkusen (DE)

(72) Inventors: Lukas Reisky, Cologne (DE); Gernot Jaeger, Cologne (DE)

(73) Assignee: Covestro Intellectual Property GmbH & Co. KG, Leverkusen (DE)

( * ) Notice: Subject to any disclaimer, the term of this patent is extended or adjusted under 35 U.S.C. 154(b) by 504 days.

(21) Appl. No.: 17/619,100

(22) PCT Filed: Aug. 10, 2020

(86) PCT No.: PCT/EP2020/072333
§ 371 (c)(1),
(2) Date: Dec. 14, 2021

(87) PCT Pub. No.: WO2021/032513
PCT Pub. Date: Feb. 25, 2021

(65) Prior Publication Data
US 2022/0259380 A1    Aug. 18, 2022

(30) Foreign Application Priority Data

Aug. 16, 2019  (EP) ..................... 19192115

(51) Int. Cl.
C08G 71/04  (2006.01)
C12N 9/80   (2006.01)
C12P 13/02  (2006.01)

(52) U.S. Cl.
CPC .............. *C08G 71/04* (2013.01); *C12N 9/80* (2013.01); *C12P 13/02* (2013.01); *C12Y 305/01075* (2013.01)

(58) Field of Classification Search
CPC ...................................... C08G 71/04
See application file for complete search history.

(56) References Cited

U.S. PATENT DOCUMENTS

| 4,336,406 A | * | 6/1982 | Gerlock | C07C 41/34 |
| | | | | 568/613 |
| 4,593,117 A | * | 6/1986 | Knofel | C08G 18/701 |
| | | | | 560/115 |
| 2021/0269834 A1 | * | 9/2021 | Bittner | C12P 13/001 |

FOREIGN PATENT DOCUMENTS

| EP | 1693409 A1 | 8/2006 |
| EP | 2825586 A2 | 1/2015 |
| WO | 2006019095 A1 | 2/2006 |

OTHER PUBLICATIONS

Xie F, Zhang T, Bryant P, Kurusingal V, Colwell JM, Laycock B, Degradation and stabilization of polyurethane elastomers, Progress in Polymer Science (2018), https://doi.org/10.1016/j.progpolymsci.2018.12.003.*
A. Magnin et al. / Waste Management 85 (2019) 141-150.*
International Search Report for International Patent Application No. PCT/EP2020/072333, mailed Oct. 23, 2020.
Written Opinion for International Patent Application No. PCT/EP2020/072333, mailed Oct. 23, 2020.
Benes et al., "Utilization of Natural Oils for Decomposition of Polyurethanes", Jul. 30, 2011, pp. 175-185.

* cited by examiner

*Primary Examiner* — Michael L Leonard
(74) *Attorney, Agent, or Firm* — K&L Gates LLP

(57) ABSTRACT

A process is provided, by means of which polyurethanes, which have been formed from polyether polyols and aromatic isocyanates, can be decomposed to polyether polyols and aromatic amines.

16 Claims, No Drawings
Specification includes a Sequence Listing.

SEQUENCE LISTING

```
<160> NUMBER OF SEQ ID NOS: 13

<210> SEQ ID NO 1
<211> LENGTH: 469
<212> TYPE: PRT
<213> ORGANISM: Unknown
<220> FEATURE:
<223> OTHER INFORMATION: Derived from metagenome

<400> SEQUENCE: 1
```

```
Met Met Gly Gly Val Gly Val Arg Glu Glu Leu Ala Thr Trp Thr Ala
1               5                   10                  15

Val Arg Leu Ala Glu His Ile Arg Lys Lys Glu Leu Ser Pro Val Glu
            20                  25                  30

Val Thr Asp Tyr Phe Leu Arg Arg Ile Glu Ala Leu Asn Pro Ala Val
            35                  40                  45

Asn Ala Phe Cys Thr Val Asp Ala Asp Gly Ala Met Arg Ala Ala Lys
        50                  55                  60

Ala Ala Glu Gln Arg Leu Met Ala Gly Glu Thr Pro Pro Leu Leu Gly
65                  70                  75                  80

Val Pro Val Ala Ile Lys Asp Leu Thr Pro Thr Lys Gly Ile Arg Thr
                85                  90                  95

Thr Tyr Gly Ser Arg Leu Phe Ala Asp Asn Val Pro Glu Ala Asp Ala
            100                 105                 110

Val Leu Val Thr Arg Leu Lys Gln Ala Gly Ala Ile Ile Val Gly Lys
            115                 120                 125

Thr Asn Thr Pro Glu Phe Gly His Ala Gly Val Thr Asp Asn Arg Leu
        130                 135                 140

Phe Gly Arg Thr Asn Asn Pro Trp Asp Leu Ser Arg Ile Ala Gly Gly
145                 150                 155                 160

Ser Ser Gly Gly Ser Asp Gly Gly Ser Ile Arg Ile Pro Ala Ser
            165                 170                 175

Cys Cys Gly Ile Phe Gly Phe Lys Pro Thr Phe Gly Arg Val Pro His
                180                 185                 190

Asp Thr Gly Ala Thr Ala Phe Ser Ile Thr Ala Pro Phe Leu His His
            195                 200                 205

Gly Pro Met Ser Arg Thr Val Glu Asp Ser Val Leu Met Leu Ala Ala
        210                 215                 220

Met Gln Gly Pro Asp Gly Cys Asp Pro Phe Ser Leu Pro Leu Pro Gly
225                 230                 235                 240

Ile Asp Trp Pro Leu Ser Ala Glu Ile Lys Pro Phe Ser Gln Trp Arg
                245                 250                 255

Ile Ala Tyr Ser Pro Asn Leu Asp Phe Tyr Ala Ile Asp Pro Ala Val
            260                 265                 270

Arg Gln Val Met Glu Gln Ala Val Ser Ala Leu Gln Gly Leu Gly Cys
            275                 280                 285

Arg Val Glu Glu Val Arg Leu Gly Leu Glu Gly Lys Thr Leu Val
        290                 295                 300

Leu Glu Thr Phe Ala Arg Leu Trp Ala Val His Tyr Ala Ala Phe Tyr
305                 310                 315                 320

Glu Glu Leu Leu Glu Arg Glu Ala Glu Leu Ser Lys Gly Phe Val Ala
                325                 330                 335

Thr Ile Arg Tyr Gly Gln Gln Phe Ser Ala Val Glu Tyr Lys Arg Leu
            340                 345                 350

Glu Arg Pro Arg Ala Val Val Tyr Glu Arg Val Glu Asn Val Phe Ala
            355                 360                 365

Lys Tyr Asp Leu Leu Ile Thr Pro Thr Leu Ala Val Pro Pro Phe Ala
        370                 375                 380

His Asp Cys Pro Pro Arg Glu Ile Asp Gly Lys Ala Val Asn Pro Tyr
385                 390                 395                 400

Asn Glu Trp Met Leu Thr Ser Ile Phe Asn Leu Thr Gly His Pro Val
                405                 410                 415

Ala Ser Ile Pro Ala Gly Phe Ser Pro Glu Gly Leu Pro Ile Gly Met
```

```
                420                 425                 430
Gln Ile Val Gly Pro Arg Leu Ala Asp Ala Ala Val Leu Glu Phe Ala
            435                 440                 445
Tyr Leu Phe Glu Gln Thr Val Ala Pro Arg Arg Pro Tyr Pro Cys Asp
        450                 455                 460
Asp Val Arg Leu Asn
465

<210> SEQ ID NO 2
<211> LENGTH: 264
<212> TYPE: PRT
<213> ORGANISM: Unknown
<220> FEATURE:
<223> OTHER INFORMATION: Derived from metagenome
<220> FEATURE:
<221> NAME/KEY: misc_feature
<222> LOCATION: (252)..(252)
<223> OTHER INFORMATION: Xaa can be any naturally occurring amino acid

<400> SEQUENCE: 2

Leu Asp Tyr Leu Gly Gly Phe Ser Pro Leu Glu Ser Asp Val Thr Val
1               5                   10                  15
Glu Lys Thr Arg Ile Ala Gly Val Pro Gly Glu Trp Ile Ser Thr Pro
            20                  25                  30
Asp Ala Arg Lys Asp Arg Val Leu Phe Tyr Leu His Gly Gly Ala Tyr
        35                  40                  45
Cys Phe Gly Ser Cys Asp Ser His Arg Gly Leu Val Ser Arg Leu Ala
    50                  55                  60
Arg Ala Cys Gly Ser Arg Ala Leu Leu Ile Glu Tyr Arg Leu Ala Pro
65                  70                  75                  80
Glu His Pro Phe Pro Ala Ala Leu Glu Asp Ser Thr Ala Ala Tyr Arg
                85                  90                  95
Glu Leu Ile Arg Ser Gly Val Arg Pro Glu Asn Leu Val Ile Ala Gly
            100                 105                 110
Asp Ser Ala Gly Gly Gly Leu Thr Met Ala Thr Leu Leu Thr Leu Arg
        115                 120                 125
Asp Glu Gly Asp Pro Leu Pro Ser Ala Ala Val Leu Leu Ser Pro Trp
    130                 135                 140
Thr Asp Leu Glu Gly Thr Gly Glu Ser Met Lys Thr Lys Ala Asp Val
145                 150                 155                 160
Glu Pro Trp Leu Asp Pro Glu Lys Ser His Leu Leu Ala Lys Leu Tyr
                165                 170                 175
Leu Gly Asp Leu Asp Pro Arg His Pro Leu Val Ser Pro Ile His Ala
            180                 185                 190
Asp Leu Asn Asn Leu Pro Pro Leu Val His Val Gly Ser Asp Glu
        195                 200                 205
Cys Leu Leu Asp Asp Ser Val Arg Leu Val Glu Arg Ala Lys Ser Ala
    210                 215                 220
Gly Val Glu Thr Glu Phe Lys Ile Cys Asp Glu Met Trp His Val Phe
225                 230                 235                 240
His Gly Phe Pro Ile Pro Glu Ala Gln Gln Ala Xaa Glu Glu Ile Gly
                245                 250                 255
Ala Phe Val Arg Ala Arg Leu Pro
            260

<210> SEQ ID NO 3
<211> LENGTH: 297
```

```
<212> TYPE: PRT
<213> ORGANISM: Unknown
<220> FEATURE:
<223> OTHER INFORMATION: Derived from metagenome

<400> SEQUENCE: 3

Met Ala Ser Pro Gln Ser Glu Ala Ile Arg Gln Met Leu Arg Glu Gln
1               5                   10                  15

Lys Glu Ala Ala Lys Lys Gly Ala Pro Ser Ile Glu Glu Gln Arg Arg
                20                  25                  30

Gln Leu Asp Tyr Leu Gly Gly Phe Ser Pro Leu Glu Ser Asp Val Thr
            35                  40                  45

Val Glu Lys Thr Arg Ile Ala Gly Val Pro Gly Glu Trp Ile Ser Thr
50                  55                  60

Pro Asp Ala Arg Lys Asp Arg Val Leu Phe Tyr Leu His Gly Gly Ala
65                  70                  75                  80

Tyr Cys Phe Gly Ser Cys Asp Ser His Arg Gly Leu Val Ser Arg Leu
                85                  90                  95

Ala Arg Ala Cys Gly Ser Arg Ala Leu Leu Ile Glu Tyr Arg Leu Ala
                100                 105                 110

Pro Glu His Pro Phe Pro Ala Ala Leu Glu Asp Ser Thr Ala Ala Tyr
            115                 120                 125

Arg Glu Leu Ile Arg Ser Gly Val Arg Pro Glu Asn Leu Val Ile Ala
130                 135                 140

Gly Asp Ser Ala Gly Gly Leu Thr Met Ala Thr Leu Leu Thr Leu
145                 150                 155                 160

Arg Asp Glu Gly Asp Pro Leu Pro Ser Ala Ala Val Leu Leu Ser Pro
                165                 170                 175

Trp Thr Asp Leu Glu Gly Thr Gly Glu Ser Met Lys Thr Lys Ala Asp
            180                 185                 190

Val Glu Pro Trp Leu Asp Pro Glu Lys Ser His Leu Leu Ala Lys Leu
            195                 200                 205

Tyr Leu Gly Asp Leu Asp Pro Arg His Pro Leu Val Ser Pro Ile His
210                 215                 220

Ala Asp Leu Asn Asn Leu Pro Leu Leu Val His Val Gly Ser Asp
225                 230                 235                 240

Glu Cys Leu Leu Asp Asp Ser Val Arg Leu Val Glu Arg Ala Lys Ser
                245                 250                 255

Ala Gly Val Glu Thr Glu Phe Lys Ile Trp Asp Glu Met Trp His Val
                260                 265                 270

Phe His Gly Phe Pro Ile Pro Glu Ala Gln Gln Ala Ile Glu Glu Ile
            275                 280                 285

Gly Ala Phe Val Arg Ala Arg Leu Pro
290                 295

<210> SEQ ID NO 4
<211> LENGTH: 311
<212> TYPE: PRT
<213> ORGANISM: Unknown
<220> FEATURE:
<223> OTHER INFORMATION: Derived from metagenome

<400> SEQUENCE: 4

Met Ala Asp Pro Gln Leu Glu Ala Val Leu Val Gly Leu Ala Gln Ala
1               5                   10                  15

Ser Ala Gly Ala Gln Gly Pro Ala Thr Val Glu Gly Phe Arg Val Ala
                20                  25                  30
```

Leu Arg Glu Leu Thr Arg Met Leu Asp Phe Arg Asp Ile Pro Val Gly
            35                  40                  45

Arg Val Glu Asn Arg Met Ile Pro Gly Pro Asp Gly Glu Ile Gly Ile
 50                  55                  60

Arg Ile Tyr Thr Pro Ile Ala Gly Ala Arg Met Leu Glu Thr Leu
 65                  70                  75                  80

Ile Tyr Phe His Gly Gly Phe Val Ala Gly Asp Leu Glu Thr His
                85                  90                  95

Asp Thr Leu Cys Arg Gly Leu Thr Ala Arg Ser Gly Cys Arg Val Ile
                100                 105                 110

Ser Val Asp Tyr Arg Leu Ala Pro Glu His Pro Phe Pro Ala Ala Ile
            115                 120                 125

Asp Asp Ser Tyr Ala Ala Leu Arg Trp Ile Glu Ala Asn Ala Thr Thr
130                 135                 140

Leu Gly Val Asp Ser Asn Arg Ile Ala Val Gly Gly Asp Ser Ala Gly
145                 150                 155                 160

Gly Asn Ile Ala Ala Val Val Ala Gln Leu Ala Arg Gly Ala Gly Asn
                165                 170                 175

Pro Val Val Arg Phe Gln Leu Leu Ile Tyr Pro Val Val Gln Trp Asp
            180                 185                 190

Val Ala Thr Pro Ser Arg Gln Gln Phe Ala Glu Asp Pro Ile Ile Pro
            195                 200                 205

Arg Asp Val Ile Asp Met Cys Ala Arg Asn Tyr Phe Gly Pro Met Val
            210                 215                 220

Pro Ala Thr Asp Phe Arg Ala Ala Pro Leu Ala Ala Ser Asp Leu Ala
225                 230                 235                 240

Gly Leu Pro Pro Ala Tyr Val Ile Thr Ala Gly Leu Asp Pro Leu Arg
                245                 250                 255

Asp Glu Gly Ala Gln Tyr Ala Glu Lys Leu Arg Glu Ala Gly Val Ala
            260                 265                 270

Val Glu His Val Gly Tyr Asp Asp Met Ile His Gly Phe Met Ser Met
            275                 280                 285

Ser Asn Ala Leu Asp Thr Ala Lys Leu Ala Ile Glu Arg Ala Gly Asp
        290                 295                 300

Ala Leu Arg Asn Ala Leu Arg
305                 310

<210> SEQ ID NO 5
<211> LENGTH: 316
<212> TYPE: PRT
<213> ORGANISM: Unknown
<220> FEATURE:
<223> OTHER INFORMATION: Derived from metagenome

<400> SEQUENCE: 5

Met Ser Leu Asp Pro Lys Ala Arg Glu Leu Leu Ala Met Val Tyr Arg
 1               5                  10                  15

Val Asn Ala Pro Arg Phe His Glu Leu Ser Val Ser Gln Ala Arg His
                20                  25                  30

Ala Thr Gln Lys Leu Met Phe Ala Phe Arg Pro Glu Ala Pro Ala Val
            35                  40                  45

Ala Ser Thr Thr Glu Val Pro Ile Pro Arg Pro Asp Gly Ser Val Leu
 50                  55                  60

Phe Ala Arg Leu Tyr Arg Pro Leu Gly Cys His Ala Ser Glu Asp Leu
 65                  70                  75                  80

```
Gly Leu Leu Ile Tyr Phe His Gly Gly Trp Cys Thr Gly Asp Leu
                85                  90                  95

Pro Gly Tyr Asp Val Leu Cys Arg Glu Leu Ala Asn Gln Ser Gly Ala
            100                 105                 110

Ala Val Leu Ser Val Asp Tyr Arg Leu Ala Pro Glu His Arg Phe Pro
        115                 120                 125

Ala Ala Val His Asp Ala Ser Leu Ala Phe Glu Trp Ser Thr Glu Asn
    130                 135                 140

Ala Ser Leu Leu Gly Val Asp Ala Glu Arg Ile Ala Leu Gly Gly Asp
145                 150                 155                 160

Ser Ala Gly Gly Asn Leu Ala Ile Val Ala Ala Leu Glu Ala Arg Asp
                165                 170                 175

Arg Ala Ala Arg Met Pro Arg Ala Leu Ala Leu Ile Tyr Pro Ser Thr
            180                 185                 190

Gln Ile His Ser Glu Arg Ser Ser Arg Glu Thr Phe Ala Asp Gly Tyr
        195                 200                 205

Phe Leu Asp Arg Glu Ser Leu Arg Trp Phe Tyr Glu His Tyr Phe Ala
    210                 215                 220

Asp Pro Ala Gln Ala Gln Ser Trp Gln Ala Ser Pro Met Leu Ala Ala
225                 230                 235                 240

Ser Leu Ala Gly Leu Pro Pro Ala Ile Leu Ile Thr Ala Gly Cys Asp
                245                 250                 255

Pro Leu Thr Asp Asp Cys Val Ala Phe Ala Glu Arg Met Val Ala Asp
            260                 265                 270

Gly Gly Leu Val Val Arg His His Phe Glu Gly Met Val His Gly Phe
        275                 280                 285

Leu Pro Leu Gly Lys Phe Phe Ala Gln Ala Asn Glu Ala Val Arg Cys
    290                 295                 300

Val Ser Ser Tyr Leu Arg Glu Ala Leu Gln Ala Ser
305                 310                 315

<210> SEQ ID NO 6
<211> LENGTH: 297
<212> TYPE: PRT
<213> ORGANISM: Unknown
<220> FEATURE:
<223> OTHER INFORMATION: Derived from metagenome
<220> FEATURE:
<221> NAME/KEY: misc_feature
<222> LOCATION: (216)..(216)
<223> OTHER INFORMATION: Xaa can be any naturally occurring amino acid

<400> SEQUENCE: 6

Met Ser Leu Glu Glu Leu Ala Val Val Arg Gln Leu Leu Ala Gly Leu
1               5                   10                  15

Val Thr Gly Glu Ala Arg Ser Leu Glu Asp Phe Arg Thr Ser Tyr Asp
            20                  25                  30

Glu Ala Gly Lys Ala Phe Gly Leu Pro Glu Gly Val Thr Val Thr Pro
        35                  40                  45

Val Ser Ala Gly Gly Val Pro Gly Glu Trp Leu Ala Pro Ala Ala Gly
    50                  55                  60

Ala Gly Lys Arg Val Leu Leu Tyr Leu His Gly Gly Tyr Ala Leu
65                  70                  75                  80

Gly Ser Leu Asp Ser His Arg His Leu Ala Ala His Thr Ala Leu Ala
                85                  90                  95

Leu Asn Gly Arg Val Leu Leu Ile Asp Tyr Arg Arg Ser Pro Glu His
```

```
            100                 105                 110
Pro Phe Pro Ala Ala Val Asp Asp Ala Leu Ala Ala Tyr Arg Trp Leu
        115                 120                 125

Thr Glu Thr Gly Val Asp Pro Ala Lys Leu Ala Val Ala Gly Asp Ser
        130                 135                 140

Ala Gly Gly Gly Leu Thr Val Ala Val Leu Ala Ala Arg Asp Ala
145                 150                 155                 160

Gly Leu Arg Leu Pro Ala Ala Val Cys Ile Ser Pro Trp Ala Asn
                165                 170                 175

Leu Glu Asn Lys Gly Ala Ser Tyr Gly Ala Lys Ala Asn Val Asp Pro
                180                 185                 190

Met Val Arg His Ala Asp Leu Glu Leu Trp Thr Ala Ala Tyr Leu Gly
        195                 200                 205

Thr Ser Thr Pro Arg Arg Ala Xaa Leu Ala Ser Pro Val Tyr Ala Asp
        210                 215                 220

Leu Asn Gly Leu Pro Pro Phe Leu Ile Gln Val Gly Ser Ser Glu Val
225                 230                 235                 240

Leu Leu Ser Asp Ser His Leu Leu Ala Asp Arg Leu Lys Glu Ala Gly
                245                 250                 255

Val Ser Val Asp Leu His Val Trp Pro Glu Met Ile His Val Trp His
                260                 265                 270

Trp Phe Ala Pro Val Leu Ser Glu Gly Arg Ala Ala Ile Asp Glu Met
        275                 280                 285

Ala Ser Phe Leu Asp Thr Lys Leu Gly
        290                 295

<210> SEQ ID NO 7
<211> LENGTH: 490
<212> TYPE: PRT
<213> ORGANISM: Unknown
<220> FEATURE:
<223> OTHER INFORMATION: Derived from metagenome

<400> SEQUENCE: 7

Met Thr Gly Leu His Phe Arg Ser Ala Ser Glu Leu Gly Arg Met Ile
1               5                   10                  15

Arg Arg Gly Glu Ile Ser Ser Ala Glu Leu Thr Asp His Phe Ile Gln
            20                  25                  30

Arg Ile Glu Thr Leu Asp Gly Lys Thr Asn Ala Val Val Ala Arg Asp
        35                  40                  45

Phe Asp Arg Ala Arg Ala Leu Ala Lys Glu Ala Asp Ala Ala Gln Ala
    50                  55                  60

Arg Gly Ala Ser Leu Gly Ala Leu His Gly Leu Pro Phe Thr Ile Lys
65                  70                  75                  80

Asp Ala Tyr Glu Val Glu Gly Ile Val Ser Thr Gly Gly Asn Pro Thr
                85                  90                  95

Trp Lys Asp His Val Pro Thr Ser Ser Ala Thr Ala Val Glu Arg Leu
            100                 105                 110

Gln Arg Ser Gly Ala Ile Val Met Gly Lys Thr Asn Val Pro Tyr Leu
        115                 120                 125

Ser Gly Asp Leu Gln Thr Tyr Asn Asp Ile Tyr Gly Thr Thr Asn Asn
    130                 135                 140

Pro Trp Ala Leu Asp Cys Gly Pro Gly Gly Ser Ser Gly Gly Ser Ala
145                 150                 155                 160

Ala Ser Leu Ala Ala Gly Phe Ala Ala Ala Glu Phe Gly Ser Asp Ile
```

```
                165                 170                 175
Gly Gly Ser Ile Arg Thr Pro Ala His Leu Cys Gly Val Phe Gly His
            180                 185                 190

Lys Pro Ser Phe Gly Ile Val Pro Lys Arg Gly His Leu Ser Pro Pro
            195                 200                 205

Pro Gly Cys Leu Ser Glu Gly Asp Leu Ser Val Ala Gly Pro Leu Ala
            210                 215                 220

Arg Ser Ala Glu Asp Leu Lys Leu Leu Ser Leu Thr Ala Gly Pro
225                 230                 235                 240

Asp Trp Ala Asp Ala Ala Gly Trp Lys Leu Asp Leu Pro Pro Ala Arg
                245                 250                 255

Ala Arg Thr Pro Arg Glu Leu Arg Ala Ala Val Trp Ile Asp Asp Glu
                260                 265                 270

Phe Cys Asp Ile Asp Arg Glu Ser Ala Asp Leu Leu Arg Asn Ala Ala
                275                 280                 285

Lys Ala Leu Gln Asp Ala Gly Ala Asn Val Asp Trp Asn Ala Arg Pro
290                 295                 300

Asp Phe Thr Leu Ala Glu Ile Thr Glu Cys Tyr Leu Ile Leu Leu His
305                 310                 315                 320

Ser Gln Ile Gly Ala Gly Met Pro Gln Ser Ile Arg Asp His Trp Ala
                325                 330                 335

Glu Met Lys Lys Gly Phe Ala Pro Asp Asp Lys Ser His Ala Ala Leu
                340                 345                 350

Gln Ala Ile Gly Gly Thr Leu Ser Leu Ala Glu Arg Ala Val Trp Lys
                355                 360                 365

Glu Val Gln Ala Gln Leu Arg Trp Lys Trp His Thr Phe Phe Lys Ser
370                 375                 380

Tyr Asp Val Val Leu Ser Pro Val Leu Met Arg Pro Ala Phe Glu His
385                 390                 395                 400

Asn His Gln Ser Asn Trp His Lys Arg Glu Leu Asp Val Asn Gly Val
                405                 410                 415

Lys Arg Pro Tyr Met Asp Val Leu Ile Trp Ala Gly Pro Ala Val Val
                420                 425                 430

Ser Tyr Leu Pro Ala Thr Ala Ala Pro Val Gly Val Thr Ser Glu Gly
                435                 440                 445

Lys Pro Val Gly Ile Gln Ile Ile Gly Pro His Leu Glu Asp Tyr Thr
                450                 455                 460

Thr Ile Ala Val Ala Gly Met Phe Glu Glu Ile Leu Gly Gly Phe Lys
465                 470                 475                 480

Pro Pro Lys Gly Trp Ala Ala Ala Leu Glu
                485                 490

<210> SEQ ID NO 8
<211> LENGTH: 177
<212> TYPE: PRT
<213> ORGANISM: Unknown
<220> FEATURE:
<223> OTHER INFORMATION: Derived from metagenome

<400> SEQUENCE: 8

Cys Ala Cys Cys Leu Ser Leu Val Asp Arg Asp Gly Arg Arg Pro Gly
1               5                   10                  15

Glu Leu Ala Val Ala Gly Asp Ser Ala Gly Gly Gly Leu Thr Val Ala
                20                  25                  30

Val Leu Leu Ala Ala Arg Asp Ala Gly Leu Arg Leu Pro Ala Ala Ala
```

```
                35                  40                  45
Val Cys Ile Ser Pro Trp Ala Asn Leu Glu Asn Lys Gly Ala Ser Tyr
 50                  55                  60

Gly Ala Lys Ala Asn Val Asp Pro Met Val Arg His Ala Asp Leu Glu
 65                  70                  75                  80

Leu Trp Thr Ala Ala Tyr Leu Gly Thr Ser Thr Pro Arg Arg Ala Pro
                 85                  90                  95

Leu Ala Ser Pro Val Tyr Ala Asp Leu Asn Gly Leu Pro Pro Phe Leu
                100                 105                 110

Ile Gln Val Gly Ser Ser Glu Val Leu Leu Ser Asp Ser His Leu Leu
                115                 120                 125

Ala Asp Arg Leu Lys Glu Ala Gly Val Ser Val Asp Leu His Val Trp
                130                 135                 140

Pro Glu Met Ile His Val Trp His Trp Phe Ala Pro Val Leu Ser Glu
145                 150                 155                 160

Gly Arg Ala Ala Ile Asp Glu Met Ala Ser Phe Leu Asp Thr Lys Leu
                165                 170                 175

Gly

<210> SEQ ID NO 9
<211> LENGTH: 491
<212> TYPE: PRT
<213> ORGANISM: Unknown
<220> FEATURE:
<223> OTHER INFORMATION: Derived from metagenome

<400> SEQUENCE: 9

Leu Glu Arg Ser Asp Leu Asp Tyr Ala Ser Ala Thr Glu Ile Ala Arg
 1               5                  10                  15

Leu Val Arg Thr Arg Gln Ile Ser Ala Ala Asp Val Thr Glu His Ala
                20                  25                  30

Ile Ser Arg Ile Glu Ala Arg Asn Gly Ser Leu Asn Ala Phe Val Tyr
                35                  40                  45

Thr Asp Phe Glu Gln Ala Arg Ser Arg Ala Lys Asp Leu Asp Thr Arg
 50                  55                  60

Ile Ser Ala Gly Glu Asp Val Gly Pro Leu Ala Gly Val Pro Thr Ala
 65                  70                  75                  80

Ile Lys Asp Leu Phe Asn Phe Tyr Pro Gly Trp Pro Ser Thr Leu Gly
                 85                  90                  95

Gly Ile Arg Cys Leu Arg Asp Phe Lys Leu Asp Val Lys Ser Arg Tyr
                100                 105                 110

Ala Thr Lys Met Glu Glu Ala Gly Ala Val Val Leu Gly Ile Thr Asn
                115                 120                 125

Ser Pro Val Leu Gly Phe Arg Gly Thr Thr Asp Asn Asp Leu Tyr Gly
                130                 135                 140

Pro Thr Arg Asn Pro Phe Asp Leu Ser Arg Asn Ser Gly Gly Ser Ser
145                 150                 155                 160

Gly Gly Thr Ser Ala Ala Val Ala Asp Gly Leu Leu Pro Ile Gly Asp
                165                 170                 175

Gly Thr Asp Gly Gly Ser Ile Arg Ile Pro Ala Ala Trp Cys His
                180                 185                 190

Val Phe Gly Phe Gln Ala Ser Pro Gly Arg Ile Pro Leu Ala Ile Arg
                195                 200                 205

Pro Asn Ala Phe Gly Ala Ala Pro Phe Ile Tyr Glu Gly Pro Ile
210                 215                 220
```

Thr Arg Thr Val Glu Asp Ala Leu Ala Met Ser Val Leu Ala Gly
225                 230                 235                 240

Ser Asp Pro Ala Asp Pro Phe Ser Leu Asn Asp Arg Leu Asp Trp Leu
            245                 250                 255

Gly Ala Val Asp Gln Pro Ile Thr Ser Leu Arg Ile Gly Phe Thr Pro
        260                 265                 270

Asp Phe Gly Gly Phe Pro Val Glu Pro Ala Val Ala Ala Thr Ile Ala
    275                 280                 285

His Ala Val Arg Ala Phe Glu Gln Ala Gly Ala Lys Ile Val Pro Leu
290                 295                 300

Lys Leu Asp Phe Gly Tyr Thr His Asp Glu Leu Ser Gln Leu Trp Cys
305                 310                 315                 320

Arg Met Ile Ser Gln Gly Thr Ile Ala Val Val Asp Ser Phe Ala Glu
                325                 330                 335

Asn Gly Leu His Leu Glu Pro Asp Phe Pro Ala Pro Val Met Glu Trp
            340                 345                 350

Ala Gln Lys Ala Lys Asn Ala Thr Pro Leu Asp Leu His Arg Asp Gln
        355                 360                 365

Val Met Arg Thr Lys Val Tyr Asp Val Leu Asn Ala Ala Phe Ser Gln
    370                 375                 380

Val Asp Leu Ile Ala Gly Pro Thr Thr Thr Cys Leu Pro Thr Pro Asn
385                 390                 395                 400

Gly Glu Arg Gly Met Thr Val Gly Pro Ser Glu Ile Ala Gly Thr Pro
                405                 410                 415

Ile Asn Arg Leu Ile Gly Phe Cys Pro Thr Phe Leu Thr Asn Phe Thr
            420                 425                 430

Gly Asn Pro Ala Ala Ser Leu Pro Ala Gly Leu Ala Asp Gly Leu Pro
        435                 440                 445

Val Gly Leu Met Leu Ile Gly Pro Arg Asp Asp Leu Thr Val Leu
    450                 455                 460

Ser Ala Ser Ala Ala Phe Glu Arg Val Gln Pro Trp Ala Asp Ser Tyr
465                 470                 475                 480

Arg Ile Pro Ala Ala Arg Pro Leu Gly Ser Gln
                485                 490

<210> SEQ ID NO 10
<211> LENGTH: 330
<212> TYPE: PRT
<213> ORGANISM: Unknown
<220> FEATURE:
<223> OTHER INFORMATION: Derived from metagenome

<400> SEQUENCE: 10

Met Arg Pro Arg Ser Arg Pro His Ala Arg Ala Arg Gly Ala Pro Thr
1               5                   10                  15

Ile Leu Arg Asp Pro Ala Thr Met Ala Leu His Arg Thr Pro Arg Arg
            20                  25                  30

Asn Asp Met Ala Asp Arg Gly Ile Glu Val Val His Ala His Leu Ala
        35                  40                  45

Lys Leu Pro Pro Ala Asp Ser Leu Thr Val Ala Glu Arg Arg Ala Gln
    50                  55                  60

Tyr Glu Arg Ala Glu Lys Val Phe Pro Leu Ser Pro Asp Val Lys Val
65                  70                  75                  80

Glu Arg Val Thr Ala Gly Ala Ala Pro Ala Glu Trp Leu Arg Pro Pro
                85                  90                  95

```
Ser Ala Arg Ala Gly His Val Val Leu Tyr Leu His Gly Gly Gly Tyr
            100                 105                 110

Val Ile Gly Ser Pro Arg Ser His Arg His Leu Ala Ala Ala Ile Ala
            115                 120                 125

Gly Ala Ala Gly Thr Asn Ala Leu Leu Leu Asp Tyr Arg Leu Ala Pro
130                 135                 140

Glu His Pro Phe Pro Ala Ala Leu Asp Asp Ala Val Ala Ala Tyr Arg
145                 150                 155                 160

Trp Leu Leu Asp Gln Gly Ile Ala Ala Glu His Ile Ala Val Ala Gly
                165                 170                 175

Asp Ser Ala Gly Gly Leu Thr Val Ala Thr Leu Leu Ala Leu Arg
            180                 185                 190

Asp Ala His Leu Pro Arg Pro Ala Ala Gly Val Cys Ile Ser Pro Trp
            195                 200                 205

Val Asp Leu Thr Cys Ser Gly Gly Ser Tyr Gln Ser Lys Ala Gly Val
210                 215                 220

Asp Pro Ile Val Arg Gln Ala Gly Val Ala Glu Met Ala Arg Ala Tyr
225                 230                 235                 240

Leu Gly Ala Thr Asp Pro Arg Ser Pro Leu Ala Ser Pro Leu Phe Ala
                245                 250                 255

Asp Leu Arg Gly Leu Pro Pro Leu Leu Ile His Val Gly Ser Asp Glu
            260                 265                 270

Val Leu Leu Asp Asp Ala Ile Gly Leu Ala Glu Arg Ala Lys Ala Ala
            275                 280                 285

Gly Val Asp Ala Thr Leu Glu Gln Trp Asp Arg Met Ile His Val Trp
290                 295                 300

His Trp Phe Leu Pro Met Leu Asp Glu Ala Gln Thr Ala Val Glu Ser
305                 310                 315                 320

Ile Gly Arg Phe Val Arg Ala Arg Thr Ala
                325                 330

<210> SEQ ID NO 11
<211> LENGTH: 544
<212> TYPE: PRT
<213> ORGANISM: Pig

<400> SEQUENCE: 11

Gly Gln Pro Ala Ser Pro Pro Val Val Asp Thr Ala Gln Gly Arg Val
1               5                   10                  15

Leu Gly Lys Tyr Val Ser Leu Glu Gly Leu Ala Gln Pro Val Ala Val
            20                  25                  30

Phe Leu Gly Val Pro Phe Ala Lys Pro Pro Leu Gly Ser Leu Arg Phe
        35                  40                  45

Ala Pro Pro Gln Pro Ala Glu Pro Trp Ser Phe Val Lys Asn Thr Thr
50                  55                  60

Ser Tyr Pro Pro Met Cys Cys Gln Asp Pro Val Ala Gly Gln Met Thr
65                  70                  75                  80

Ser Asp Leu Phe Thr Asn Arg Lys Glu Arg Leu Ile Pro Glu Phe Ser
                85                  90                  95

Glu Asp Cys Leu Tyr Leu Asn Ile Tyr Thr Pro Ala Asp Leu Thr Lys
            100                 105                 110

Arg Gly Arg Leu Pro Val Met Val Trp Ile His Gly Gly Gly Leu Val
            115                 120                 125

Val Gly Gly Ala Ser Thr Tyr Asp Gly Leu Ala Leu Ala Ala His Glu
```

```
            130                 135                 140
Asn Val Val Val Ala Ile Gln Tyr Arg Leu Gly Ile Trp Gly Phe
145                 150                 155                 160

Phe Ser Thr Gly Asp Glu His Ser Arg Gly Asn Trp Gly His Leu Asp
            165                 170                 175

Gln Val Ala Ala Leu His Trp Val Gln Glu Asn Ile Ala Asn Phe Gly
            180                 185                 190

Gly Asp Pro Gly Ser Val Thr Ile Phe Gly Glu Ser Ala Gly Gly Glu
            195                 200                 205

Ser Val Ser Val Leu Val Leu Ser Pro Leu Ala Lys Asn Leu Phe His
210                 215                 220

Arg Ala Ile Ser Glu Ser Gly Val Ala Phe Thr Ala Gly Leu Val Arg
225                 230                 235                 240

Lys Asp Met Lys Ala Ala Lys Gln Ile Ala Val Leu Ala Gly Cys
                245                 250                 255

Lys Thr Thr Thr Ser Ala Val Phe Val His Cys Leu Arg Gln Lys Ser
                260                 265                 270

Glu Asp Glu Leu Leu Asp Leu Thr Leu Lys Met Lys Phe Ala Leu
            275                 280                 285

Asp Leu His Gly Asp Pro Arg Glu Ser His Pro Phe Leu Thr Thr Val
            290                 295                 300

Val Asp Gly Val Leu Leu Pro Lys Met Pro Glu Glu Ile Leu Ala Glu
305                 310                 315                 320

Lys Asp Phe Asn Thr Val Pro Tyr Ile Val Gly Ile Asn Lys Gln Glu
                325                 330                 335

Phe Gly Trp Leu Leu Pro Thr Met Met Gly Phe Pro Leu Ser Glu Gly
            340                 345                 350

Lys Leu Asp Gln Lys Thr Ala Thr Ser Leu Leu Trp Lys Ser Tyr Pro
            355                 360                 365

Ile Ala Asn Ile Pro Glu Glu Leu Thr Pro Val Ala Thr Asp Lys Tyr
            370                 375                 380

Leu Gly Gly Thr Asp Asp Pro Val Lys Lys Lys Asp Leu Phe Leu Asp
385                 390                 395                 400

Leu Met Gly Asp Val Val Phe Gly Val Pro Ser Val Thr Val Ala Arg
                405                 410                 415

Gln His Arg Asp Ala Gly Ala Pro Thr Tyr Met Tyr Glu Phe Gln Tyr
            420                 425                 430

Arg Pro Ser Phe Ser Ser Asp Lys Lys Pro Lys Thr Val Ile Gly Asp
            435                 440                 445

His Gly Asp Glu Ile Phe Ser Val Phe Gly Ala Pro Phe Leu Arg Gly
450                 455                 460

Asp Ala Pro Glu Glu Glu Val Ser Leu Ser Lys Thr Val Met Lys Phe
465                 470                 475                 480

Trp Ala Asn Phe Ala Arg Ser Gly Asn Pro Asn Gly Glu Gly Leu Pro
                485                 490                 495

His Trp Pro Met Tyr Asp Gln Glu Glu Gly Tyr Leu Gln Ile Gly Val
            500                 505                 510

Asn Thr Gln Ala Ala Lys Arg Leu Lys Gly Glu Glu Val Ala Phe Trp
            515                 520                 525

Asn Asp Leu Leu Ser Lys Glu Ala Ala Lys Lys Pro Pro Lys Ile Lys
530                 535                 540
```

<210> SEQ ID NO 12

```
<211> LENGTH: 342
<212> TYPE: PRT
<213> ORGANISM: Candida sp.

<400> SEQUENCE: 12

Met Lys Leu Leu Ser Leu Thr Gly Val Ala Gly Val Leu Ala Thr Cys
1               5                   10                  15

Val Ala Ala Thr Pro Leu Val Lys Arg Leu Pro Ser Gly Ser Asp Pro
            20                  25                  30

Ala Phe Ser Gln Pro Lys Ser Val Leu Asp Ala Gly Leu Thr Cys Gln
        35                  40                  45

Gly Ala Ser Pro Ser Ser Val Ser Lys Pro Ile Leu Leu Val Pro Gly
    50                  55                  60

Thr Gly Thr Thr Gly Pro Gln Ser Phe Asp Ser Asn Trp Ile Pro Leu
65                  70                  75                  80

Ser Thr Gln Leu Gly Tyr Thr Pro Cys Trp Ile Ser Pro Pro Pro Phe
                85                  90                  95

Met Leu Asn Asp Thr Gln Val Asn Thr Glu Tyr Met Val Asn Ala Ile
            100                 105                 110

Thr Ala Leu Tyr Ala Gly Ser Gly Asn Asn Lys Leu Pro Val Leu Thr
        115                 120                 125

Trp Ser Gln Gly Gly Leu Val Ala Gln Trp Gly Leu Thr Phe Phe Pro
    130                 135                 140

Ser Ile Arg Ser Lys Val Asp Arg Leu Met Ala Phe Ala Pro Asp Tyr
145                 150                 155                 160

Lys Gly Thr Val Leu Ala Gly Pro Leu Asp Ala Leu Ala Val Ser Ala
                165                 170                 175

Pro Ser Val Trp Gln Gln Thr Thr Gly Ser Ala Leu Thr Thr Ala Leu
            180                 185                 190

Arg Asn Ala Gly Gly Leu Thr Gln Ile Val Pro Thr Thr Asn Leu Tyr
        195                 200                 205

Ser Ala Thr Asp Glu Ile Val Gln Pro Gln Val Ser Asn Ser Pro Leu
    210                 215                 220

Asp Ser Ser Tyr Leu Phe Asn Gly Lys Asn Val Gln Ala Gln Ala Val
225                 230                 235                 240

Cys Gly Pro Leu Phe Val Ile Asp His Ala Gly Ser Leu Thr Ser Gln
                245                 250                 255

Phe Ser Tyr Val Val Gly Arg Ser Ala Leu Arg Ser Thr Thr Gly Gln
            260                 265                 270

Ala Arg Ser Ala Asp Tyr Gly Ile Thr Asp Cys Asn Pro Leu Pro Ala
        275                 280                 285

Asn Asp Leu Thr Pro Glu Gln Lys Val Ala Ala Ala Leu Leu Ala
    290                 295                 300

Pro Ala Ala Ala Ile Val Ala Gly Pro Lys Gln Asn Cys Glu Pro
305                 310                 315                 320

Asp Leu Met Pro Tyr Ala Arg Pro Phe Ala Val Gly Lys Arg Thr Cys
                325                 330                 335

Ser Gly Ile Val Thr Pro
            340

<210> SEQ ID NO 13
<211> LENGTH: 472
<212> TYPE: PRT
<213> ORGANISM: Rhodococcus hoagii

<400> SEQUENCE: 13
```

-continued

```
Met Asn Thr Ser Gly Leu Gly Trp Met Ser Ala Thr Glu Met Ala Ala
1               5                   10                  15

Gln Val Ala Ser Lys Lys Leu Ser Pro Asn Glu Ile Ala Glu Glu Met
            20                  25                  30

Ile Arg Arg Val Gly Glu Val Asn Pro Ser Val Asn Ala Ile Val His
        35                  40                  45

Phe Asp Ala Asp Gln Val Arg Arg Asp Ala Gly Glu Leu Thr Arg Ala
    50                  55                  60

Gln Asp Ser Gly Glu Pro Leu Gly Pro Leu His Gly Val Pro Phe Thr
65                  70                  75                  80

Ile Lys Asp Leu Thr Asp Val Arg Gly Leu Pro Thr Thr Phe Gly Leu
                85                  90                  95

Lys Pro Met Arg Asp Asn Ile Ala Glu Arg Asp Ala Val Ile Val Thr
            100                 105                 110

Arg Leu Arg Gln Ala Gly Gly Leu Tyr Leu Gly Lys Thr Asn Thr Pro
        115                 120                 125

Glu Ser Gly Tyr Tyr Gly Gly Thr Asp Asn His Leu Phe Gly Pro Thr
    130                 135                 140

His Asn Pro Trp Lys Pro Gly His Ser Ala Gly Gly Ser Ser Gly Gly
145                 150                 155                 160

Ala Ala Ala Ala Val Ala Ala Gly Leu Gly Pro Leu Ala Glu Gly Ser
                165                 170                 175

Asp Gly Ala Gly Ser Val Arg Ile Pro Ser Ala Leu Cys Gly Val Val
            180                 185                 190

Gly Leu Lys Pro Thr Thr Gly Val Ile Pro Gln Thr Ile Leu Pro Gly
        195                 200                 205

Arg Tyr Asn Asn Trp Ala Tyr His Gly Pro Ile Thr Arg Thr Val Ala
    210                 215                 220

Asp Asn Ala Leu Met Leu Asp Val Leu Ala Gly Pro Asp His Ser Asp
225                 230                 235                 240

Pro Leu Ser Ile Glu Arg Val Glu Ser Ser Tyr Val Glu Ala Ala Arg
                245                 250                 255

Gly Gly Ile Asp Gly Leu Arg Val Ala Trp Ser Pro Asn Leu Gly Leu
            260                 265                 270

Gly His Val Glu Pro Asp Val Ala Ala Val Cys Ala Glu Ala Val Ala
        275                 280                 285

Cys Phe Glu Asp Met Gly Ala Lys Val Val Glu Ala Thr Pro Asp Trp
    290                 295                 300

Gly Asp Pro Ser Glu Ala Met Trp His Gly Ile Trp Val Pro Gly Phe
305                 310                 315                 320

Ala Gly Glu His Asp Met Leu Asp Trp Asp Ser Leu His Gly Gln Val
                325                 330                 335

Asp Asp Asn Leu Ile Glu Leu Ile His Glu Gly Arg Arg Leu Thr Gly
            340                 345                 350

Val Asp Tyr Gly Arg Ala Asp Ala Phe Arg Gly Arg Met Trp Asp Thr
        355                 360                 365

Trp Thr Glu Phe Met Asn Asp Tyr Asp Val Leu Ile Ser Pro Thr Leu
    370                 375                 380

Ala Ser Ala Thr Phe Pro Leu Thr Gln Phe Ala Pro Asp Trp Leu Gln
385                 390                 395                 400

Gly Lys Ser Leu Arg Glu Gln Leu Leu Asp Trp Leu Leu Thr Tyr Pro
                405                 410                 415
```

```
                                    -continued

Tyr Asn Met Leu Asn Asn Pro Ala Ile Thr Val Pro Ala Gly Phe Thr
            420             425             430

Ala Asp Gly Arg Pro Val Gly Leu Gln Ile Ala Ala Arg His Arg Gln
        435             440             445

Asp Ala Leu Val Leu Arg Val Ala Ala Asn Leu Glu Gln Ala Arg Pro
    450             455             460

Trp Ala Asp Arg Arg Pro Val Ala
465             470
```

PROCESS FOR THE DECOMPOSITION OF POLYETHER-POLYURETHANE

CROSS REFERENCE TO RELATED APPLICATIONS

This application is a U.S. national stage application, filed under 35 U.S.C. § 371, of International Application No. PCT/EP2020/072333, which was filed on Aug. 10, 2020, and which claims priority to European Patent Application No. 19192115.4 which was filed on Aug. 16, 2019. The contents of each are hereby incorporated by reference into this specification.

FIELD

The present invention relates to a process with which polyurethanes formed from polyether polyols and isocyanates can be broken down into polyether polyols and amines.

BACKGROUND

Polyurethanes are used in large amounts inter alia in the production of hard and soft foams. When these materials are burned at the end of their service life, $CO_2$ is evolved. Since the raw materials for the production of polyurethanes are produced predominantly or entirely from crude oil, the combustion of polyurethanes leads to an increase in the $CO_2$ content of the atmosphere. It is therefore highly desirable for polyurethane waste materials to be recycled as comprehensively as possible.

Polyurethanes are formed from an isocyanate component and a polyol component. These undergo an addition reaction to form the urethane group that connects the two components, thereby forming the polymer network. Foam production uses predominantly isocyanates having aromatically attached isocyanate groups, in particular tolylene diisocyanate, methylene diphenyl isocyanate, and multiring derivatives of methylene diphenyl isocyanate. Commonly used as the polyol component are polyether polyols.

Processes already exist for the recovery of polyether polyols from polyurethanes, some of which are already being tested on an industrial scale. These processes are based on reaction of the polyurethane with low-molecular-weight alcohols such as glycol. In such processes, an exchange of the polyether polyol for the low-molecular-weight alcohol takes place. This exchange of a polyol that is part of a urethane group for another polyol is referred to in the present patent application, by analogy with a transesterification, as a "transurethanization". Reaction products of such a transurethanization are the polyether used to produce the polyurethane and a urethane derived from the aromatic polyisocyanate used to synthesize the polyurethane and the low-molecular-weight alcohol used for the transurethanization. The newly formed urethane is of low molecular weight, since the transurethanization uses the low-molecular-weight polyol in a large molar excess in relation to the polyether content of the polyurethane, and consequently a large proportion of the low-molecular-weight polyol molecules react only with one molecule derived from the isocyanate used to produce the polyether polyurethane. Details and variants of this process are given in Simon et al. (2018), Waste Management, 76: 147-171.

However, only the polyether polyol liberated by the polyurethane is recycled. The low-molecular-weight urethane formed in the course of the transurethanization is a by-product for which there is not as yet any satisfactory use. Simon et al. (2014), Journal of Material Cycles and Waste Management, 16: 523-525 describe a process in which the unreacted low-molecular-weight alcohol was removed from the urethanization product by distillation. The distillation residue consisted of a poorly defined mixture of aromatic amines and low-molecular-weight urethanes. This residue could be used as an initiator for the synthesis of polyether polyols. For use of the distillation residue in other fields of application, the multiplicity of compounds present therein is disadvantageous.

In a mirror image of the process described above, Beneš, H., Černá, R., Ďuračková, A., & Látalová, P. (2012). Utilization of natural oils for decomposition of polyurethanes. Journal of Polymers and the Environment, 20(1), 175-185 describe a process in which fish oil or castor oil are used as alcohols for the transurethanization. The aim of this process is to obtain the low-molecular-weight urethane as a starting material for further chemical reactions. Since the alcohols used are strongly hydrophobic, this product is at the end of the process present in a phase together with the liberated polyether.

SUMMARY

The object of the present invention was to provide a process that enables polyether polyurethanes to be broken down as completely as possible into compounds that are chemically defined as exactly as possible.

This object is achieved by a process comprising the steps of
  a) transurethanizing a polyether polyurethane with at least one low-molecular-weight alcohol to form polyether polyols and low-molecular-weight urethanes; and
  b) enzymatically cleaving the low-molecular-weight urethanes formed in process step a), with liberation of at least one amine and the at least one low-molecular-weight alcohol used in process step a).

Process step a) has two aims: (i) The polyether polyol used to synthesize the polyurethane should be liberated from the polyurethane as an isolable compound. (ii) The isocyanate used to synthesize the polyurethane should be present as a constituent of a low-molecular-weight urethane. In contrast to polyurethane with its high molecular weight, said low-molecular-weight urethane is on account of its lower molecular weight and consequent better solubility well suited as a substrate for the enzymatic cleavage that takes place in process step b).

In process step b), an amine and the low-molecular-weight alcohol used for transurethanization in process step a) are liberated by enzymatic cleavage of low-molecular-weight urethanes. In addition, $CO_2$ is evolved in this process step. These compounds can be isolated by suitable methods of separation and then used further. Here, it is preferable for the liberated low-molecular-weight alcohol to be reused for the transurethanization that takes place in process step a). The liberated amine is available as a pure and well-defined starting material for new syntheses.

DETAILED DESCRIPTION

Polyether Urethane

A polyurethane is a compound formed from polyols and polyisocyanates. The entirety of all polyols used to form the polyurethane is also referred to in this patent application as the "polyol component". The entirety of all the polyisocyanates used to form the polyurethane is referred to in the present patent application as the "isocyanate component".

One hydroxyl group of each polyol forms a urethane group with one isocyanate group of each polyisocyanate through an addition reaction, thereby crosslinking the structural components of the polyurethane.

The polyurethane to be broken down by the process of the invention is a polyether polyurethane. This term refers to polyurethanes in which the polyol component comprises polyether polyols. Preferably, at least 40% by weight of the hydroxyl groups present in the polyol component are constituents of polyether polyols. More preferably, this is at least 60% by weight, even more preferably at least 80% by weight, and most preferably at least 95% by weight. It is in accordance with the invention possible for a polyether polyurethane to also contain further polyols as structural components while maintaining the abovementioned proportions of polyether polyols. These are preferably polyester polyols.

Isocyanate groups can in principle also react with other functional groups that contain Zerewitinoff-active hydrogen atoms. Such functional groups are in particular amino groups and thiol groups. In this case, the addition reaction gives rise respectively to urea groups and thiourethane groups. However, in a "polyether urethane" according to the present patent application the proportion of urethane linkages and urea linkages in the total amount of urethane linkages, urea linkages, and thiourethane linkages is at least 60 mol %, preferably at least 80 mol %, and more preferably at least 90 mol %. The proportion of urethane linkages in relation to the total amount of urethane linkages, urea linkages, and thiourethane linkages is at least 20 mol %, preferably at least 40 mol %, and more preferably at least 60 mol %.

In addition, a "polyurethane" has for the purposes of the present patent application at least 3, preferably at least 5, urethane groups per molecule. The resulting crosslinking of a plurality of molecules of the structural components involved leads to the polyurethane having a high molecular weight. The number-average molecular weight of a polyurethane to be broken down by the process of the invention is accordingly preferably at least 1350 g/mol.

Polyether Polyol

The term "polyether polyol" is well known to those skilled in the art. These are polyethers having an average hydroxyl functionality of between 1.5 and 6.0. The polyether polyol present in the polyether polyurethane is preferably a polyaddition product of one or more alkylene oxides having 2 to 4 carbon atoms using at least one starter molecule containing 2 to 8, preferably 2 to 6, attached reactive hydrogen atoms.

Preferred alkylene oxides are styrene oxide, ethylene oxide, propylene oxide, tetrahydrofuran, butylene oxide, and epichlorohydrin. Greater preference is given to 1,3-propylene oxide, 1,2- or 2,3-butylene oxide, and styrene oxide. Particular preference is given to ethylene oxide and 1,2-propylene oxide. The alkylene oxides may be used singly, alternately in succession, or as mixtures.

Preferred starter molecules for the polyaddition are water, organic dicarboxylic acids, aliphatic and aromatic, optionally N-mono-, N,N-, or N,N'-dialkyl-substituted, diamines having 1 to 4 carbon atoms in the alkyl radical, dihydric alcohols, and polyhydric alcohols.

Preferred organic dicarboxylic acids are succinic acid, adipic acid, phthalic acid, and terephthalic acid.

Preferred diamines are mono- and dialkyl-substituted ethylenediamine, diethylenetriamine, triethylenetetramine, propylene-1,3-diamine, butylene-1,3-diamine or -1,4-diamine, hexamethylene-1,2-diamine, -1,3-diamine, -1,4-diamine, -1,5-diamine and -1,6-diamine, phenylenediamines, tolylene-2,3-diamine, -2,4-diamine, and -2,6-diamine, and 2,2'-, 2,4'-, and 4,4'-diaminodiphenylmethane.

Preferred dihydric and polyhydric alcohols are ethanediol, propane-1,2- and -1,3-diol, diethylene glycol, dipropylene glycol, butane-1,4-diol, hexane-1,6-diol, triethanolamine, bisphenols, glycerol, trimethylolpropane, pentaerythritol, sorbitol, and sucrose.

Isocyanate

Polyurethanes in which the isocyanate component comprises isocyanates having aliphatically, cycloaliphatically, aromatically or araliphatically attached isocyanate groups are in principle suitable for breakdown by the process of the invention.

In an isocyanate having aliphatically attached isocyanate groups, all isocyanate groups are attached to a carbon atom that is part of an open carbon chain. This may be unsaturated in one or more positions. The aliphatically attached isocyanate group or—in the case of polyisocyanates—aliphatically attached isocyanate groups are preferably attached at the terminal carbon atoms of the carbon chain.

Polyisocyanates having aliphatically attached isocyanate groups that are in accordance with the invention particularly suitable are 1,4-diisocyanatobutane (BDI), 1,5-diisocyanatopentane (PDI), 1,6-diisocyanatohexane (HDI), 2-methyl-1,5-diisocyanatopentane, 1,5-diisocyanato-2,2-dimethylpentane, 2,2,4- or 2,4,4-trimethyl-1,6-diisocyanatohexane, and 1,10-diisocyanatodecane.

In an isocyanate having cycloaliphatically attached isocyanate groups, all isocyanate groups are attached to carbon atoms that are part of a closed ring of carbon atoms. This ring may be unsaturated in one or more positions, provided it does not acquire aromatic character as a result of the presence of double bonds.

Polyisocyanates having cycloaliphatically attached isocyanate groups that are in accordance with the invention particularly suitable are 1,3- and 1,4-diisocyanatocyclohexane, 1,4-diisocyanato-3,3,5-trimethylcyclohexane, 1,3-diisocyanato-2-methylcyclohexane, 1,3-diisocyanato-4-methylcyclohexane, 1-isocyanato-3,3,5-trimethyl-5-isocyanatomethylcyclohexane (isophorone diisocyanate; IPDI), 1-isocyanato-1-methyl-4(3)-isocyanatomethylcyclohexane, 2,4'- and 4,4'-diisocyanatodicyclohexylmethane (H12MDI), 1,3- and 1,4-bis(isocyanatomethyl)cyclohexane, bis(isocyanatomethyl)norbornane (NBDI), 4,4'-diisocyanato-3,3'-dimethyldicyclohexylmethane, 4,4'-diisocyanato-3,3',5,5'-tetramethyldicyclohexylmethane, 4,4'-diisocyanato-1,1'-bi(cyclohexyl), 4,4'-diisocyanato-3,3'-dimethyl-1,1'-bi(cyclohexyl), 4,4'-diisocyanato-2,2',5,5'-tetramethyl-1,1'-bi(cyclohexyl), 1,8-diisocyanato-p-menthane, 1,3-diisocyanatoadamantane, and 1,3-dimethyl-5,7-diisocyanatoadamantane.

In an isocyanate having araliphatically attached isocyanate groups, all isocyanate groups are attached to methylene radicals that are in turn attached to an aromatic ring.

Polyisocyanates having araliphatically attached isocyanate groups that are in accordance with the invention particularly suitable are 1,3- and 1,4-bis(isocyanatomethyl) benzene (xylylene diisocyanate; XDI), 1,3- and 1,4-bis(1-isocyanato-1-methylethyl)benzene (TMXDI), and bis(4-(1-isocyanato-1-methylethyl)phenyl) carbonate.

The polymerizable composition may in accordance with the invention comprise any desired mixtures of the abovementioned isocyanates in monomeric and/or oligomeric form.

In an isocyanate having aromatically attached isocyanate groups, all isocyanate groups are attached directly to carbon atoms that are part of an aromatic ring.

Isocyanates having aromatically attached isocyanate groups that are in accordance with the invention particularly suitable are tolylene diisocyanate (TDI), methylene diphenyl isocyanate (MDI) and naphthylene diisocyanate.

The term "tolylene diisocyanate" refers to tolylene-2,4-diisocyanate (2,4-TDI), tolylene-2,6-diisocyanate (2,6-TDI), and also any desired mixtures of the two isomers. The term "methylene diphenyl isocyanate" refers to all isomers of MDI, in particular diphenylmethane 2,2'-diisocyanate, diphenylmethane 2,4'-diisocyanate, diphenylmethane 4,4'-diisocyanate, all mixtures containing at least two of the abovementioned isomers, and also multiring derivatives of MDI.

The term "naphthylene diisocyanate" refers to naphthylene-1,4-diamine, naphthylene-1,5-diamine, and naphthylene-1,6-diamine and also any desired mixtures of the abovementioned isomers.

Preference is however given to breaking down polyether polyurethanes in which the isocyanate component comprises isocyanates having aromatically attached isocyanate groups or consisting of such isocyanates.

The isocyanate component of the polyether polyurethane particularly preferably comprises TDI, MDI or any desired mixtures of the two abovementioned isocyanates.

In a particularly preferred embodiment of the present invention, at least 50 mol % of the isocyanate groups present in the isocyanate component are a constituent of TDI and/or MDI. More preferably this is at least 65 mol % and even more preferably at least 80 mol %.

Low-molecular-weight Alcohol

Any compound having at least one hydroxyl group per molecule is in principle suitable for use as a low-molecular-weight alcohol in process step a). For the success of the overall process, certain properties of the low-molecular-weight alcohol are however advantageous, which means that low-molecular-weight alcohols meeting one or more of the conditions defined below are preferably used.

In order for the low-molecular-weight urethane from process step a) to be suitable as a substrate for enzymatic cleavage of the urethane linkage, the molecular weight of the low-molecular-weight alcohol must not be too high. This is preferably not more than 700 g/mol, more preferably not more than 500 g/mol, and most preferably not more than 200 g/mol.

It is additionally advantageous to use low-molecular-weight alcohols, the urethanes of which form separate phases with the polyether polyol liberated from the polyether urethane. It is also possible to use here low-molecular-weight alcohols, the esters of which form separate phases after addition of a further solvent. This promotes the formation of a separate polyether phase, thereby allowing the liberated polyether polyol to be easily separated from the reaction mixture. For this reason, preference is given to low-molecular-weight alcohols having relatively high polarity. Preferably, the low-molecular-weight alcohol contains at least 2 hydroxyl groups per molecule. Particularly preferably, the low-molecular-weight alcohol contains at least 2 hydroxyl groups per molecule and has a molecular weight of not more than 500 g/mol, more preferably not more than 200 g/mol.

Low-molecular-weight alcohols having a low melting point are in addition particularly suitable from a technical viewpoint, so that there is no risk of them solidifying in the pipelines of the system and causing them to block. Preference is therefore given to using low-molecular-weight alcohols having a melting point of not more than 45° C. More preferably, the low-molecular-weight alcohols used have a melting point of not more than 20° C.

The at least one low-molecular-weight alcohol is preferably selected from the group consisting of methanol, ethanol, ethylene glycol, diethylene glycol, propylene glycol, dipropylene glycol, methyl glycol, triethylene glycol, glycerol, 2-methylpropane-1,3-diol, butane-1,4-diol, pentane-1,5-diol, hexane-1,6-diol, polyethylene glycol 400, and mixtures of two or more of the abovementioned alcohols. More preferably, it is selected from the group consisting of ethylene glycol, diethylene glycol, propylene glycol, dipropylene glycol, methyl glycol, triethylene glycol, and mixtures of two or more of the abovementioned alcohols. Very particular preference is given to the low-molecular-weight alcohol diethylene glycol.

Reaction Products

In the first process step, a free polyether is formed, which can be separated from the reaction mixture by physical methods.

If a low-molecular-weight alcohol of sufficiently high polarity is used, a two-phase mixture forms. The less polar phase consists largely of the polyether. The other, more polar phase contains the unused low-molecular-weight alcohol, low-molecular-weight urethanes, and reaction by-products, in particular aromatic amines The removal of the polyether polyol is here particularly straightforward.

The chemical structure of the resulting low-molecular-weight urethanes is determined by the reactants used in process step a). The urethanes contain a first hydrocarbon radical derived from the isocyanate component used to synthesize the polyether polyurethane. The second hydrocarbon radical is derived from the low-molecular-weight alcohol used in process step a). The two hydrocarbon radicals are linked by a urethane group, the nitrogen atom of which is attached to the first hydrocarbon radical.

Reaction Conditions

The reaction conditions and catalysts suitable in principle for the transurethanization are described in Simon et al. (2018), Waste Management, 76: 147-171. Process step a) is carried out at temperatures of between 140° C. and 300° C., preferably of between 160° C. and 270° C. The weight ratio of the low-molecular-weight alcohol to the polyether urethane is between 2:1 and 1:17. Particularly suitable as catalysts are alkali metal hydroxides, alkaline earth metal hydroxides, alkali metal salts of carboxylic acids (in particular acetates), alkaline earth metal salts of carboxylic acids (in particular acetates), Lewis acids (such as in particular dibutyltin dilaurate), organic amines (such as in particular diethanolamine), organometallic compounds (in particular titanium butoxide), and tin compounds (such as in particular tin octoate). The transurethanization is preferably performed at temperatures within a range from 160° C. to 270° C. in the presence of 0.1% by mass to 5% by mass of catalyst, based on the mass of polyurethane product added.

Enzymatic Cleavage

In addition to the actual enzymatic cleavage of the low-molecular-weight urethane, process step b) can also comprise further substeps. These serve in particular to improve the efficiency of the enzymatic cleavage.

Since the urethane cleavage is a hydrolysis, it is preferable to add water to the product obtained in process step a).

In a preferred embodiment, the liberated polyether polyols are first separated from the product obtained in process step a) before the enzyme used for the enzymatic cleavage is added.

However, it is also possible to carry out the enzymatic cleavage in a mixture that still contains the liberated polyether polyols.

In a further preferred embodiment, the excess alcohol, i.e. alcohol that has not been incorporated into low-molecular-weight urethane, is removed before the enzyme is added. This can be achieved particularly advantageously by distillation.

In a further preferred embodiment, at least one cosolvent and/or at least one detergent is added in process step b). This can increase the solubility of the low-molecular-weight urethane in water and thus improve its accessibility for the enzyme. Preferred cosolvents are ethanol, acetone, dimethyl sulfoxide, and dimethylformamide A preferred detergent is sorbate.

The low-molecular-weight urethane may after the urethanization also be contaminated by salts that interfere with the enzymatic cleavage. Therefore, in a further preferred embodiment of the present invention the salts present alongside the low-molecular-weight urethane are completely or partly removed before the enzyme used for the enzymatic cleavage is added.

Since low-molecular-weight alcohols in many cases have no adverse effect on the activity of the enzyme, it is also possible to omit this preparatory step in many cases. The extent to which removal of the free low-molecular-weight alcohol is necessary before the enzymatic cleavage can be determined by those skilled in the art by simple preliminary tests in the presence and absence of the low-molecular-weight alcohol used in process step a).

The enzymatic cleavage in process step b) can be carried out with any enzyme able to cleave urethane linkages.

For example, enzymes having amino acid sequences such as those defined in SEQ ID Nos. 1 to 13 are suitable for this purpose. Particularly suitable is the enzyme defined by SEQ ID No. 3 or a variant thereof. When using the abovementioned enzymes, a pH 7 reaction buffer containing 100 mM $K_2HPO_4/KH_2PO_4$ and 20% by volume of ethanol is well suited for the enzymatic cleavage of the low-molecular-weight urethane. However, it has been found that good results can also be achieved without using ethanol.

An "enzyme variant" is preferably obtained by adding, deleting or replacing up to 10%, more preferably up to 5%, of the amino acids present in the respective polypeptide. The abovementioned modifications may in principle be executed continuously or discontinuously at any desired point in the polypeptide.

However, they are preferably executed only at the N-terminus and/or at the C-terminus of the polypeptide. Each variant obtained by adding, replacing or deleting amino acids in accordance with the invention is, however, characterized by urethanase activity. This is preferably demonstrated by the test method described in example 1.

Further enzymes that are in principle suitable are described in WO 2006/019095, WO/2013/134801, Shigeno et al. (2006), Applied Microbiology and Biotechnology, 70: 422-429, Gamerith et al. (2016), Polymer Degradation and Stability, 132: 69-77, and Magnin et al. (2019), Waste Management, 85: 141-150.

The reaction products arising from the enzymatic cleavage of the low-molecular-weight urethane in process step b) are the at least one low-molecular-weight alcohol used in process step a) and an amine or mixture of amines The chemical structure of the amines formed depends on the nature of the isocyanate component used to synthesize the polyurethane Amines are liberated, which can be derived from the isocyanates used in the isocyanate component by addition of water and subsequent elimination of $CO_2$.

The process of the invention thus provides compounds having well-defined structures that are suitable as starting materials for novel syntheses of high-value products.

The working examples that follow serve solely to illustrate the invention. They are not intended to limit the scope of protection of the patent claims in any way.

WORKING EXAMPLES

Example 1 (Inventive)

Procedure:

Model Substrates for the Enzyme Reaction

Enzymes presumed to have urethanase activity were tested in the hydrolysis of exemplary urethane model compounds in order to characterize the substrate spectrum. This was done using carbamates, which can be formed during the glycolysis of polyurethanes. All model substrates used for this purpose and also the screening substrates are shown below. Reaction buffer (100 mM $KH_2PO_4/K_2HPO4$, pH 7.0) was mixed with 20% (v/v) ethanol and 0.2 mg/mL of substrate. The reactions were carried out in 200 µL test runs in glass tubes with addition of 1-3 mg of enzyme lyophilizate. The test runs were incubated with shaking for approx. 20 h at room temperature and then for approx. 16 h at 37° C. After incubation, the plates were left unagitated at room temperature to allow sedimentation of suspended particles (5 min) and the supernatant was centrifuged for 5 min at 4000 rpm and 20° C. in a large-capacity centrifuge into a 96-well polypropylene plate via 96-well filter plates having a PVDF membrane and 0.2 µm pore size (Corning, Kaiserslautern). The samples were measured by HPLC using the "Dabsylamine" method in order to detect the amine formed.

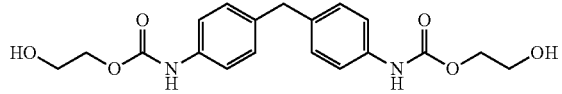

MDEC

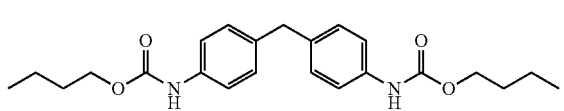

MDBC

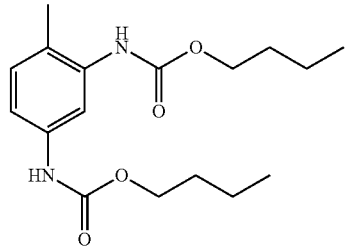

TDBC

TDMC

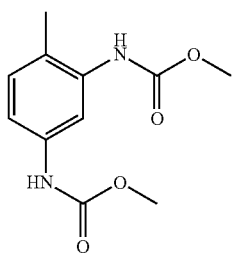

OM-3

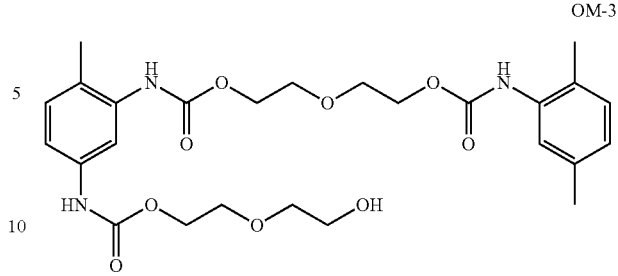

Enzyme Reactions with Oligomers from PU Foam

It was also investigated whether the urethanases are able to hydrolyze soluble oligomers formed in the hydrolysis of the ester linkages in a polyester PU foam. The glycolysis of of polyether polyurethane with diethylene glycol results in the same products. For this, 1 g of the foam was added to a 50 mL centrifuge tube with 20 mL of pH 7.0 potassium phosphate buffer and approx. 30 mg of CalB lyophilizate ("Chirazyme L2" from Roche, Basel, Switzerland) and incubated for 5 days at 37° C. and 200 rpm. The turbid solution was then centrifuged for 10 min at 25° C. and 4000 rpm in a large-capacity centrifuge. The clear supernatant was adjusted to pH 7.0 with 1 M NaOH. After about 6 h at room temperature, the slight fall in pH was retitrated to 7.0 and the solution underwent a sterilizing filtration.

This resulted in the formation of the oligomers shown below. For each oligomer mixture (OM), an isomer based on 2,4-TDA is shown by way of example, although the mixture also contains the isomers based on 2,6-TDA and also various regioisomers arising from different linking of the amino groups to diethylene glycol. Identified urethanases were tested for hydrolytic activity toward these carbamates.

The soluble oligomers were stored at 4° C. until use. 150 µL of this solution was mixed with 20 µL of DMF. To each was then added 30 µL of the undiluted, purified urethanases and the test runs were shaken on the heating block at 30° C. and 1000 rpm. A test run containing enzyme storage buffer served as the negative control. After three days, the test runs were filtered through filter plates having a PVDF membrane and a pore size of 0.2 µm (Corning, Kaiserslautern) and the filtrate was analyzed in respect of the 2,4- and 2-6-TDA formed by HPLC using the "Dabsylamine95" method.

HPLC Analysis

High-pressure liquid chromatography was carried out on an Agilent Technologies (Santa Clara, USA) 1100 series instrument equipped with an autosampler and DAD (diode array detector) for UV and the visible light region. All measurements were carried out using a Zorbax XDB-C18 column having a particle size of 3.5 µm and dimensions of 4.6×75 mm (Agilent Technologies, Santa Clara, USA). In all methods, a 5 µL sample was injected and the column heated to 40° C. The flow was generally 1.5 mL/min. Since a reverse-phase column had been used, elution in all methods was with increasing concentrations of organic solvent.

Detection and quantification of aromatic amines and urethanes was done using the "Dabsylamine" and "Dabsylamine 95" methods. Used as eluent in addition to AcN was pH 7.0 10 mM sodium phosphate buffer, to which 0.005% (w/v) sodium azide was added to protect against microbial growth. The data were analyzed using the Open-LAB CDS ChemStationLC software, version A.02.09 [017] (Agilent Technologies, Santa Clara, USA).

Dabsylamine: Eluent: Acetonitrile and 10 mM $Na_2HPO_4$/$NaH_2PO_4$, pH 7.0

| t [min] | Acetonitrile |
|---|---|
| 0 | 5 |
| 6.5 | 85 |
| 8.0 | 5 |
| 10.0 | 5 |

Dabsylamine 95: Eluent: Acetonitrile containing 5% (v/v) $ddH_2O$ and 10 mM $Na_2HPO_4$/$NaH_2PO_4$, pH 7.0

| t [min] | % Acetonitrile (+5% (v/v) $ddH_2O$) |
|---|---|
| 0 | 5 |
| 6.5 | 90 |
| 8.0 | 5 |
| 10.0 | 5 |

Results

Model Substrates for the Enzyme Reaction

The model substrates MDEC, MDBC, TDBC, and TDMC, which can be produced from polyurethanes by chemical transurethanization, were treated with active urethanases and at least one urethanase that catalyzes hydrolytic cleavage to the amine was able to be identified for each of the model substrates (Table 1). In addition, two urethanases showed activity toward oligomer mixtures OM-1, OM-2, and OM-3, with both 2,4-TDA and 2,6-TDA being liberated.

OM-1

OM-2

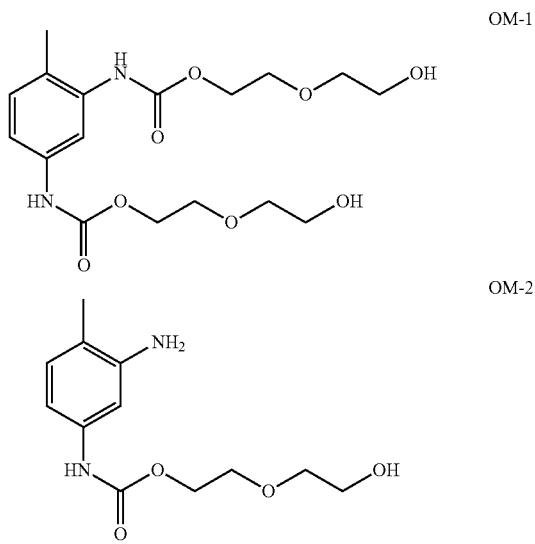

TABLE 1

Summary of the investigation of the substrate spectrum of the urethanases. Screening of further urethane compounds was done using the enzymes that showed clear activity in the screening with MDEC and also Ure.

| Enzyme | MDEC | MDBC | TDBC | TDMC | OM-1 | OM-2 | OM-3 |
|---|---|---|---|---|---|---|---|
| Ure (SEQ ID No. 13) | 0 | 0 | 0 | 1- | 0 | 0 | 0 |
| Lip250 (SEQ ID No. 9) | 1- | 0 | 0 | 3 | 0 | 0 | 0 |
| Pig liver esterase | 2- | 3- | 3- | 2 | n.d. | n.d. | n.d. |
| *Candida antarctica* lipase B | 2- | 0 | 0 | 0 | n.d. | n.d. | n.d. |
| Lip72 (SEQ ID No. 3) | n.d. | n.d. | n.d. | n.d. | 3 | 3- | 3- |
| Lip197 (SEQ ID No. 7) | n.d. | n.d. | n.d. | n.d. | 3- | 3- | 1- |

3: (almost) only completely hydrolyzed product (diamine) detectable, 2: hydrolysis to end product and intermediate product, 1: hydrolysis to intermediate product (monoamine), 0: (almost) no hydrolysis products detectable. "-" indicates that significant amounts of substrate were still present. n.d.: not determined. PLE: pig liver esterase Example 2 (inventive): Test Of Different Reaction Conditions for Carbamate Cleavage with Aes72

Introduction

This experiment sought to enzymatically hydrolyze the carbamates present in the lower phase after chemical glycolysis (transurethanization with diethylene glycol) of flexible TDI foam. Glycolysis of flexible TDI foam liberates long-chain polyether polyol that, after the reaction, settles as a second phase above the excess glycol and the carbamates and amines formed. The lower phase of the reaction product thus produced was used as substrate solution. The enzymatic hydrolysis of the urethane linkage liberates 2,4-TDA and 2,6-TDA and also diethylene glycol and $CO_2$. In example 1, cosolvents were used. Since additional solvents again need to be laboriously removed in industrial applications, tests sought to establish whether the reaction also proceeds in the absence of cosolvents. The higher the substrate concentration in the reaction, the more concentrated the TDA solution can be after the reaction, which is advantageous for subsequent processing. Aes72 (SEQ ID No. 3) was accordingly tested at substrate concentrations of up to 40% (w/v). In addition, the temperature was increased to investigate whether this has an effect on the rate of reaction.

Procedure

Chemical Glycolysis

An initial charge of 250 g of diethylene glycol was heated to 200° C. 250 g of flexible TDI foam was then metered in. Once the foam had dissolved, the temperature was kept constant for a further three hours. 2.5 g of tin(II) 2-ethylhexanoate was used as catalyst.

Enzyme Preparation

For preparation of the enzyme, E. coli BL21 (DE3) was transformed with the plasmid pET21a-Aes72. To all cultures was added 100 mg/L of ampicillin. MagicMedia (Thermofisher) was inoculated with a single colony and then incubated with shaking for 24 h at 30° C. and 130 rpm. The cells were separated off by centrifuging for 10 min at 4000 g and 4° C. The cell pellet was taken up in 10 mL of pH 7.5 50 mM potassium phosphate buffer and disrupted by sonication (amplitude 50%, pulse 1 s followed by a 1 s pause, 2 min total sonication time). After separating off the insoluble constituents by centrifugation (9500 rpm, 4° C., 20 min), the crude enzyme solution was frozen at −80° C. and then freeze-dried. The lyophilizate was stored at 4° C. In addition, a blank vector control was prepared as an enzyme preparation in which the corresponding blank vector was used instead of pET21a-Aes72.

Enzyme Reaction

Enzyme solution was prepared by dissolving 4.5% (w/v) enzyme lyophilizate in pH 7.5 50 mM potassium phosphate buffer. Each test run was prepared with a total volume of 300 µL, using 60 µL of enzyme solution and respectively 5% (w/v), 10% (w/v), 20% (w/v), and 40% (w/v) of the lower phase after glycolysis as substrate. The remainder was made up of pH 7.5 50 mM potassium phosphate buffer. These were incubated in the heating block at 40° C., 50° C. or 60° C. and 800 rpm. Reactions with a blank vector control preparation were prepared in identical manner After three hours, the total amount of TDA was quantified by HPLC. TDA concentrations in the negative controls were subtracted from the values in the enzyme reactions so as to obtain the total amount of TDA liberated by Aes72.

Stopping the Enzyme Reaction

The samples were diluted 1:2 with 50 mM NaOH in 20% acetic acid to inactivate the enzymes. The inactivated samples were incubated for at least 5 min at room temperature or for longer at 4° C. and then diluted 1:10 with 140 mM NaOH.

HPLC Analysis

The 2,4-TDA and 2,6-TDA formed were analyzed by HPLC. Standards and samples were centrifuged before analysis (2 min, 13 300 rpm, room temperature) and the supernatant was filtered through a 0.22 gm PES filter. 5 µL samples were in each case injected by the autosampler. The column used was a Zorbax Eclipse C18 (15 cm) with an appropriate guard column. Acetonitrile served as eluent A, and pH 7.0 10 mM sodium phosphate buffer as eluent B. The overall flow was 1 mL/min. The solvent gradient is shown in Table 2.

TABLE 2

| HPLC gradient | | |
|---|---|---|
| t [min] | Eluent A [%] | Eluent B [%] |
| 0.00 | 5 | 95 |
| 2.00 | 5 | 95 |
| 10.00 | 95 | 5 |
| 11.00 | 95 | 5 |
| 11.50 | 5 | 95 |
| 16.00 | 5 | 95 |

Results
The components quantified by NMR in the lower phase after chemical glycolysis are listed in Table 3.

TABLE 3

Composition of the lower phase after glycolysis. The composition was determined by ¹H-NMR measurement. The percent by weight of TDA carbamates refers solely to the TDA fraction of the compounds; the DEG fraction is shown as "Carbamated DEG".

| Component | Content |
|---|---|
| Polyol | 3.61 wt.-% |
| DEG | 67.2 wt.-% |
| TDA (diaminotoluene) | 1.92 wt.-% |
| TCA (toluene carbamate-amine) | 5.57 wt.-% |
| TDC (toluene dicarbamate) | 6.01 wt.-% |
| Carbamated DEG | 15.3 wt.-% |

The concentrations of liberated TDA under the various conditions in the enzyme reactions are shown in Table 4. It was found to be possible to achieve high conversions. It was also found that cosolvents are not essential for enzyme activity. Significant amounts of TDA are liberated at all temperatures, with the rate of reaction increasing with increasing temperature at the two lowest substrate concentrations.

TABLE 4

Total TDA liberated after 3 h. The quantified amount of TDA in the negative controls was subtracted from the amount in the enzyme reactions so as to obtain the amount of TDA liberated.

| T [° C.] | Substrate concentration [% (w/v)] | TDA liberated [g/L] |
|---|---|---|
| 40 | 5 | 2.93 |
|  | 10 | 4.05 |
|  | 20 | 2.82 |
|  | 40 | 4.80 |
| 50 | 5 | 3.78 |
|  | 10 | 4.83 |
|  | 20 | 4.51 |
|  | 40 | 5.06 |
| 60 | 5 | 4.27 |
|  | 10 | 5.07 |
|  | 20 | 4.38 |
|  | 40 | 2.39 |

Example 3 (comparison, noninventive): Replication of Beneš et al., 2012 to check phase formation Introduction The purpose of the experiment described below is to demonstrate the extent to which the carbamates described in Beneš, H., Černá, R., Duračková, A., & Látalová, P. (2012). Utilization of natural oils for decomposition of polyurethanes. Journal of Polymers and the Environment, 20(1), 175-185 are suitable as starting materials for the two-stage breakdown process disclosed in this patent application. In this process, the best-possible phase separation between the newly produced carbamate and the polyol liberated from the broken-down polyurethane is key.

According to Beneš et al., 2012, pMDI-based polyether polyurethanes undergo transurethanization with natural fats/oils, with liberation of the original polyether polyol. Since long-chain and hydrophobic oils such as castor oil are used in excess, it is unlikely that the transurethanization is followed by phase separation between the liberated polyether polyol and the newly formed carbamates and excess oil, as is employed in the present invention. To check this, the carbamates described as products by Beneš et al., 2012 were synthesized from pMDI and castor oil and a mixing test with the polyether polyol employed therein was carried out. This sought to replicate the product mixture as it exists after the glycolysis described therein.

Procedure

The product mixture from run 4BK and 4BK from Beneš et al., 2012 was to be replicated by way of example A pMDI mixture containing 32.25% NCO was used for the synthesis. 7.935 parts by weight of pMDI were added to 210 parts by weight of castor oil (10-fold OH excess) and the mixture was stirred at 80° C. until a measured NCO value of 0.03% was obtained (OH value=138.2 mg KOH/g; viscosity at 25° C.=1570 mPas). A homogeneous phase was obtained in which the MDA carbamates are completely dissolved in excess castor oil. To 26.14 g of this carbamate solution was added 11.06 g of Desmophen 5035 BT (trifunctional polypropylene ether polyol having a hydroxyl value of 35 mg KOH/g, a hydroxyl content of 1.1% by weight, and an OH equivalent weight of approx. 1600 g, manufactured by Covestro Deutschland AG, Leverkusen, Germany) (=ratio as after glycolysis in 4BK from D3).

Results

After mixing the carbamate solution and the polyether polyol, all that was observed was a homogeneous liquid phase that did not separate even after 24 h at room temperature. This shows that the process described in Beneš et al., 2012 is unsuitable for a split-phase glycolysis. Thus, it is not possible to remove the polyether polyol as a separate phase after the transurethanization, neither is a separate phase of carbamates with excess glycol that can in turn be used for the recovery of aromatic amines obtained. The process described in Beneš et al., 2012 thus in particular does not permit a two-stage cleavage of polyurethanes for the recovery of monomers than can be flexibly used. The product therein is a polyol of a particular type suitable only as a starting material for very specific reactions.

What is claimed is:

1. A process comprising the steps of
   a) transurethanizing a polyether polyurethane with at least one low-molecular-weight alcohol having at least 2 hydroxyl groups per molecule and a molecular weight of not more than 500 g/mol, to form polyether polyols and low-molecular-weight urethanes; and
   b) enzymatically cleaving the low-molecular-weight urethanes formed in process step a), with liberation of at least one amine and the at least one low-molecular-weight alcohol used in process step a).

2. The process as claimed in claim 1, wherein the isocyanate component of the polyether polyurethane comprises at least one aromatic polyisocyanate.

3. The process as claimed in claim 2, wherein the aromatic polyisocyanate is selected from the group consisting of tolylene diisocyanate, methylene diphenyl isocyanate, and naphthylene diisocyanate.

4. The process as claimed in claim 1, wherein the isocyanate component of the polyether polyurethane comprises at least one aliphatic polyisocyanate.

5. The process as claimed in claim 4, wherein the aliphatic polyisocyanate is selected from the group consisting of 1,4-diisocyanatobutane, 1,5-diisocyanatopentane, 1,6-diisocyanatohexane, 2-methyl-1,5-diisocyanatopentane, 1,5-diisocyanato-2,2-dimethylpentane, 2,2,4-or 2,4,4-trimethyl-1,6-diisocyanatohexane, 2,4'-or 4,4'-diisocyanatodicyclohexylmethane, and 1,10-diisocyanatodecane.

6. The process as claimed in claim 1, wherein at least 50% by weight of the polyol components used to form the polyether polyurethane are constituents of polyether polyols.

7. The process as claimed in claim 1, wherein a proportion of urethane linkages and urea linkages in a total amount of urethane linkages, urea linkages, and thiourethane linkages in the polyether polyurethane is at least 60 mol %.

8. The process as claimed in claim 1, wherein the at least one low-molecular-weight alcohol has at least 2 hydroxyl groups per molecule.

9. The process as claimed in claim 1, wherein the at least one low-molecular-weight alcohol has a melting point of not more than 45° C.

10. The process as claimed in claim 1, wherein the at least one low-molecular-weight alcohol is selected from the group consisting of methanol, ethanol, ethylene glycol, diethylene glycol, propylene glycol, dipropylene glycol, methyl glycol, triethylene glycol, glycerol, 2-methylpropane-1,3-diol, butane-1,4-diol, pentane-1,5-diol, hexane-1,6-diol, polyethylene glycol 400, and mixtures of two or more of the abovementioned alcohols.

11. The process as claimed in claim 10, wherein the at least one low-molecular-weight alcohol is selected from the group consisting of ethylene glycol, diethylene glycol, propylene glycol, dipropylene glycol, methyl glycol, triethylene glycol, and mixtures of two or more of the abovementioned alcohols, and is used in a molar ratio of the at least one low-molecular-weight alcohol to the polyether polyurethane such that, at the end of process step a), a phase separate from the at least one low-molecular-weight alcohol is present that contains the liberated polyether polyol.

12. The process as claimed in claim 1, wherein the low-molecular-weight urethanes are separated from the at least one low-molecular-weight alcohol before carrying out process step b).

13. The process as claimed in claim 1, wherein the at least one low-molecular-weight alcohol formed in process step b) is reused in process step a).

14. The process as claimed in claim 1, wherein at least part of the at least one low-molecular-weight alcohol liberated in process step b) is reused in process step a).

15. The process as claimed in claim 7, wherein the proportion of urethane linkages and urea linkages in the total amount of urethane linkages, urea linkages, and thiourethane linkages in the polyether polyurethane is at least 80 mol %.

16. The process as claimed in claim 15, wherein the proportion of urethane linkages and urea linkages in the total amount of urethane linkages, urea linkages, and thiourethane linkages in the polyether polyurethane is at least 90 mol %.

* * * * *